(12) United States Patent
Deutsch et al.

(10) Patent No.: US 10,143,890 B2
(45) Date of Patent: Dec. 4, 2018

(54) REMOTE CONFIGURATION AND OPERATION OF FITNESS STUDIOS FROM A CENTRAL SERVER

(71) Applicant: Fitness Engineers Pty Ltd., Bondi Beach, New South Wales (AU)

(72) Inventors: Robert Deutsch, Bondi Beach (AU); Adam Gilchrist, Queenscliff (AU)

(73) Assignee: F45 TRAINING PTY LTD, New South Wales (AU)

( * ) Notice: Subject to any disclaimer, the term of this patent is extended or adjusted under 35 U.S.C. 154(b) by 314 days.

(21) Appl. No.: 14/931,920

(22) Filed: Nov. 4, 2015

(65) Prior Publication Data

US 2016/0121162 A1 May 5, 2016

(30) Foreign Application Priority Data

Nov. 4, 2014 (AU) .................................. 2014904426

(51) Int. Cl.
| | |
|---|---|
| A63B 24/00 | (2006.01) |
| G09B 19/00 | (2006.01) |
| G06F 17/30 | (2006.01) |
| G06F 19/00 | (2018.01) |
| G16H 40/67 | (2018.01) |

(Continued)

(52) U.S. Cl.
CPC ...... *A63B 24/0062* (2013.01); *A63B 24/0075* (2013.01); *G06F 17/3074* (2013.01); *G06F 19/00* (2013.01); *G09B 19/0038* (2013.01); *G16H 20/30* (2018.01); *G16H 40/67* (2018.01); *G05G 9/047* (2013.01)

(58) Field of Classification Search
CPC ............ A63B 24/0062; A63B 24/0075; G06F 19/3481; G06F 17/3074; G09B 19/0038; G05G 9/047
See application file for complete search history.

(56) References Cited

U.S. PATENT DOCUMENTS

| | | |
|---|---|---|
| 6,050,924 A | 4/2000 | Shea |
| 8,047,965 B2 | 11/2011 | Shea |

(Continued)

FOREIGN PATENT DOCUMENTS

| | | |
|---|---|---|
| WO | 2003079134 A2 | 9/2003 |
| WO | 2014036159 A2 | 3/2014 |

*Primary Examiner* — Sundhara Ganesan
(74) *Attorney, Agent, or Firm* — Nexsen Pruet, PLLC; E. Eric Mills

(57) ABSTRACT

A method for configuring and operating one or more fitness studios each comprising a plurality of exercise stations at which users perform associated exercise routines, each station having an associated display, the method comprising, for each fitness studio, periodically retrieving, by a server from a database, fitness information for the studio in question for a specified period, from a multi-period fitness library; communicating, by the server to a studio computer, the retrieved fitness information over a communications network; periodically receiving, by the studio computer, the retrieved fitness information; configuring the exercise stations dependent upon the received fitness information; and communicating, by the studio computer to the exercise station displays, dependent upon the received fitness information, station directions to users exercising at the stations for performing an exercise.

9 Claims, 14 Drawing Sheets

(51) Int. Cl.
*G16H 20/30* (2018.01)
*G05G 9/047* (2006.01)

(56) References Cited

U.S. PATENT DOCUMENTS

| | | | |
|---|---|---|---|
| 2006/0058156 A1* | 3/2006 | Cohen | A63B 24/00 482/4 |
| 2006/0205566 A1* | 9/2006 | Watterson | A63B 24/0084 482/8 |
| 2007/0033069 A1* | 2/2007 | Rao | A63B 24/00 705/2 |
| 2008/0045384 A1* | 2/2008 | Matsubara | A63B 21/00181 482/4 |
| 2012/0040799 A1* | 2/2012 | Jaquish | A63B 21/00047 482/9 |
| 2014/0067097 A1 | 3/2014 | Harris et al. | |
| 2015/0190677 A1* | 7/2015 | Alsalem | A63B 24/0075 700/91 |

* cited by examiner

REMOTE CONFIGURATION AND OPERATION OF FITNESS STUDIOS FROM A CENTRAL SERVER

REFERENCE TO RELATED PATENT APPLICATION(S)

This application claims the benefit under 35 U.S.C. § 119 of the filing date of Australian Patent Application No. 2014904426, filed on 4 Nov. 2014, hereby incorporated by reference in its entirety as if fully set forth herein.

TECHNICAL FIELD

The present invention relates generally to fitness and exercise equipment and, in particular, to a method and system for remote configuration and operation of fitness studios from a central server.

BACKGROUND

People today are increasingly concerned with attainment and maintenance of physical fitness and wellbeing. Physical fitness studios can provide equipment and training facilities to enable people to achieve physical fitness goals, provided that users of the studios can maintain the necessary motivation.

SUMMARY

Disclosed are arrangements, referred to as Distributed Periodically Varied, Studio Configuration (DPVSC) arrangements, which download from a central server to a plurality of remote exercise studios, periodic exercise routines which vary different exercise parameters in order to improve the novelty of the exercise environment and thus improve the effectiveness thereof.

According to a first aspect of the present invention, there is provided a computer implemented method for configuring and operating one or more fitness studios each comprising a plurality of exercise stations at which users perform associated exercise routines, each exercise station having an associated display, the method comprising, for each fitness studio, the steps of: periodically retrieving, by a server from a database, studio information for the studio in question for a specified period, from a multi-period fitness library; communicating, by the server to a studio computer, the retrieved studio information over a communications network; periodically receiving, by the studio computer, the retrieved studio information; configuring the exercise stations dependent upon the received studio information; and communicating, by the studio computer to the exercise station displays, dependent upon the received studio information, station directions to users exercising at the stations for performing an exercise.

According to a second aspect of the present invention, there is provided a computer implemented method for configuring and operating a fitness studio comprising a plurality of exercise stations at which users perform associated exercise routines, each exercise station having an associated display, the method comprising the steps of: periodically receiving, by a studio computer, studio specific studio information for a specified period, from a multi-period fitness library stored on a server database; configuring the exercise stations dependent upon the received studio information; and communicating, by the studio computer to the exercise station displays, dependent upon the received studio information, station directions for users exercising at the stations for performing an exercise.

According to another aspect of the present invention, there is provided an apparatus for implementing any one of the aforementioned methods.

According to another aspect of the present invention, there is provided a computer program product including a computer readable medium having recorded thereon a computer program for implementing any one of the methods described above.

Other aspects of the invention are also disclosed.

BRIEF DESCRIPTION OF THE DRAWINGS

At least one embodiment of the present invention will now be described with reference to the drawings, in which.

DETAILED DESCRIPTION INCLUDING BEST MODE

Figure 1:
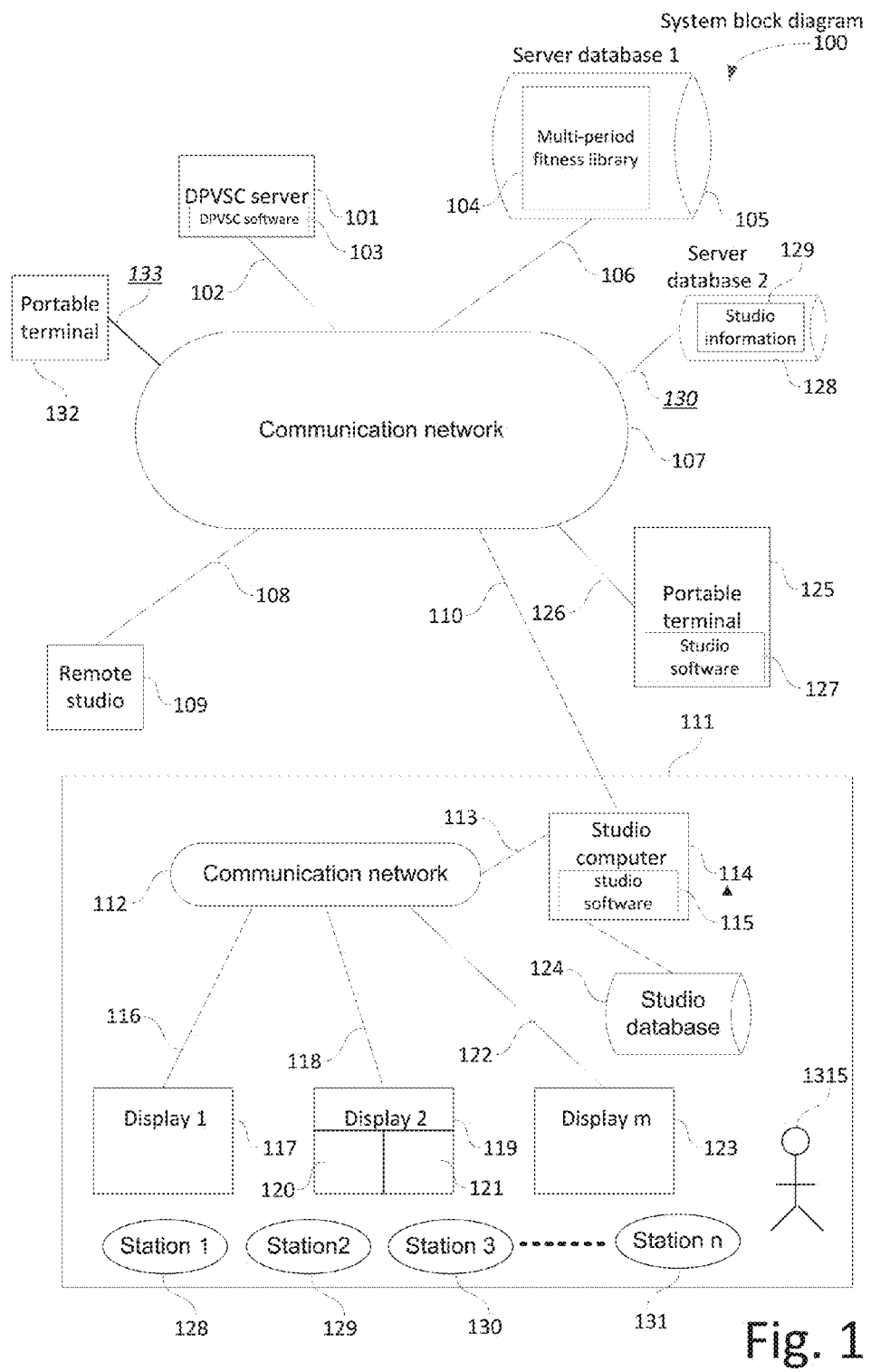
FIG. 1 is a block diagram depicting one example of a system upon which the disclosed DPVSC arrangements can be performed.

Where reference is made in any one or more of the accompanying drawings to steps and/or features, which have the same reference numerals, those steps and/or features have for the purposes of this description the same function(s) or operation(s), unless the contrary intention appears.

It is to be noted that the discussions contained in the "Background" section and that above relating to prior art arrangements relate to discussions of documents or devices which form public knowledge through their respective publication and/or use. Such should not be interpreted as a representation by the present inventor(s) or the patent applicant that such documents or devices in any way form part of the common general knowledge in the art.

FIG. 1 is a block diagram depicting one example 100 of a system upon which the disclosed DPVSC arrangements can be performed. A DPVSC server 101 communicates, using a communication network 107, with a number of fitness studios 109, 111 by means of the associated studio computers such as 114. Each studio 111 has a local communication network 112 enabling the studio computer 114 to communicate with a number of displays 117 that are distributed throughout the studio 111. These displays may, as depicted by a display 119, have a number of individually addressable display windows 120, 121. Exercise stations 128, 129, 130 . . . 131 are distributed throughout the studio 111, and each station such as 128 is located within easy view, and thus associated, with a display 117 or a display window 120.

In operation, the exercise stations 128 and their associated fitness equipment (eg a high bar 1207 in FIG. 12) if any, are physically distributed throughout the studio 111 on a periodic basis. The periodic distribution (also referred to as configuration) can be performed on any convenient and desirable basis, eg daily, weekly, or other. The configuration is typically performed on a daily basis, and the remainder of this description will refer to daily reconfiguration. This is clearly merely one example, and is not limiting.

The daily reconfiguration is based, for each studio, upon daily current studio information 213 (eg see 213 in FIG. 2) that is downloaded by the server 101 from a multi-period fitness library 104 stored in a data base 105. The daily current studio information 213 provides daily variation along a number of different dimensions, including the type of exercise performed, the equipment used, the location of the associated exercise stations within the studio, the work times and rest times associated with each exercise, the number of repetitions and so on. This daily variation helps maintain the interest and motivation of the studio users such as 1315, with the intention of increasing the likelihood that the users will maintain an ongoing program of exercise routines.

While in some DPVSC examples the displays 117, 119, 123 may be rearranged throughout the studio 111 on a daily basis, typically the stations 128, 129 . . . 130, 131 are rearranged while the displays such as 117 remain fixed in their positions. Users performing fitness routines at the exercise stations 128 are instructed, implicitly by proximity of the stations 128 to associated displays 117, or by other means such as information 1205 (see FIG. 12) on the displays, or by training staff in the studio (not shown), to direct their attention to respective displays (such as 117) or display windows (such as 120) in order to receive instructions directing them how to perform each exercise of their corresponding exercise routine.

Figure 10:
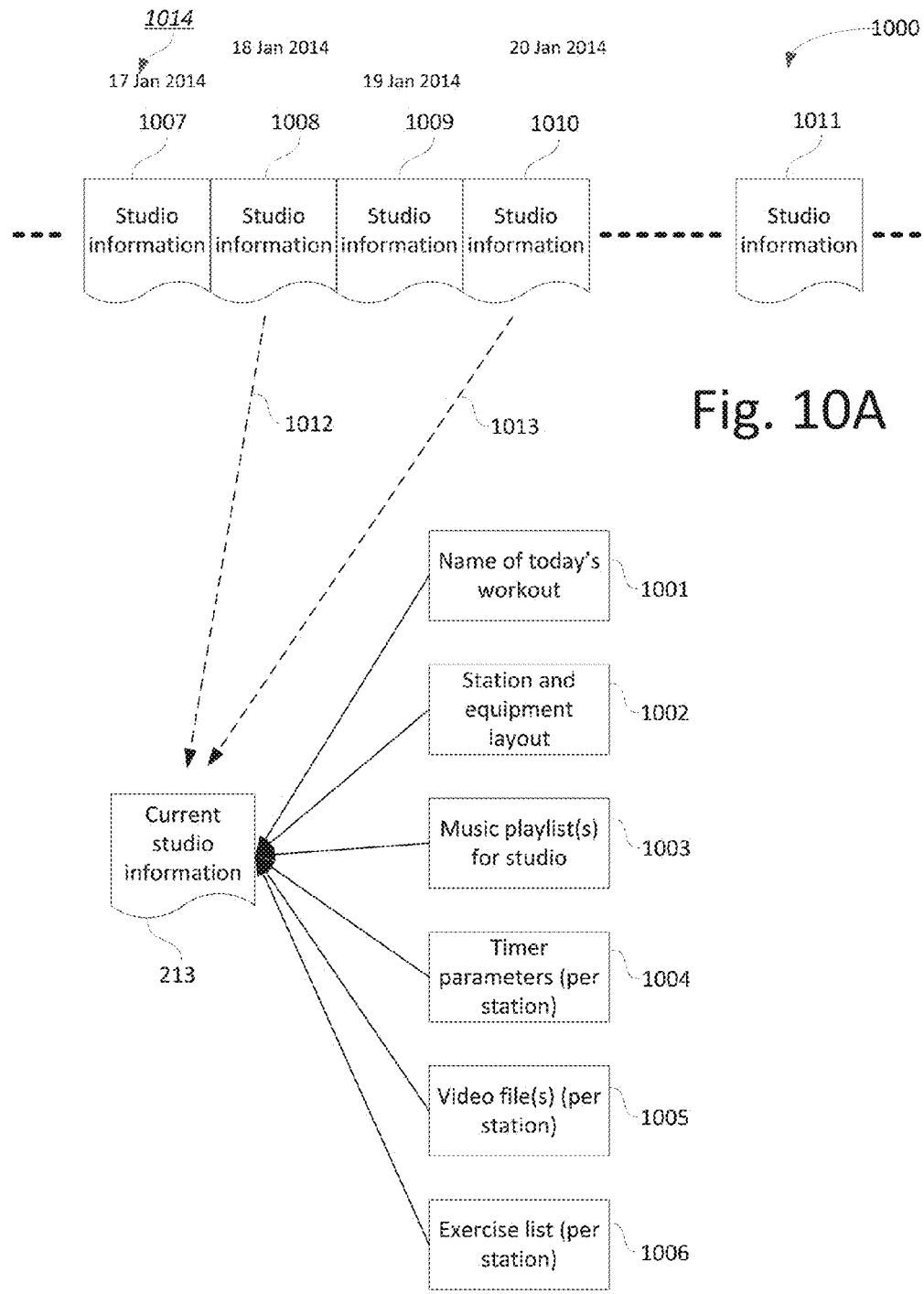
FIGS. 10A and 10B respectively depict examples of a multi-period fitness library and a current studio program extracted from the multi-period fitness library.

The DPVSC server 101 executes a DPVSC software application 103 in order to perform the disclosed DPVSC methods. As described hereinafter in more detail with respect to FIG. 10, the daily studio-specific fitness information 213 is extracted from a multi-period fitness library file 104 that is stored on the DPVSC server database 105.

Inter-studio variation is achieved, in some DPVSC arrangements, because each studio typically registers with a DPVSC service on a different date. In one DPVSC example, described hereinafter in more detail with reference to FIG. 10, the initial registration date dictates which studio specific fitness information 213 is downloaded by the DPVSC server 101 to the studio. Dates upon which studios register with the DPVSC arrangement in the program are, in the example shown in FIG. 1, stored in a studio information file 129 that is stored on a database 128.

Figure 4A:
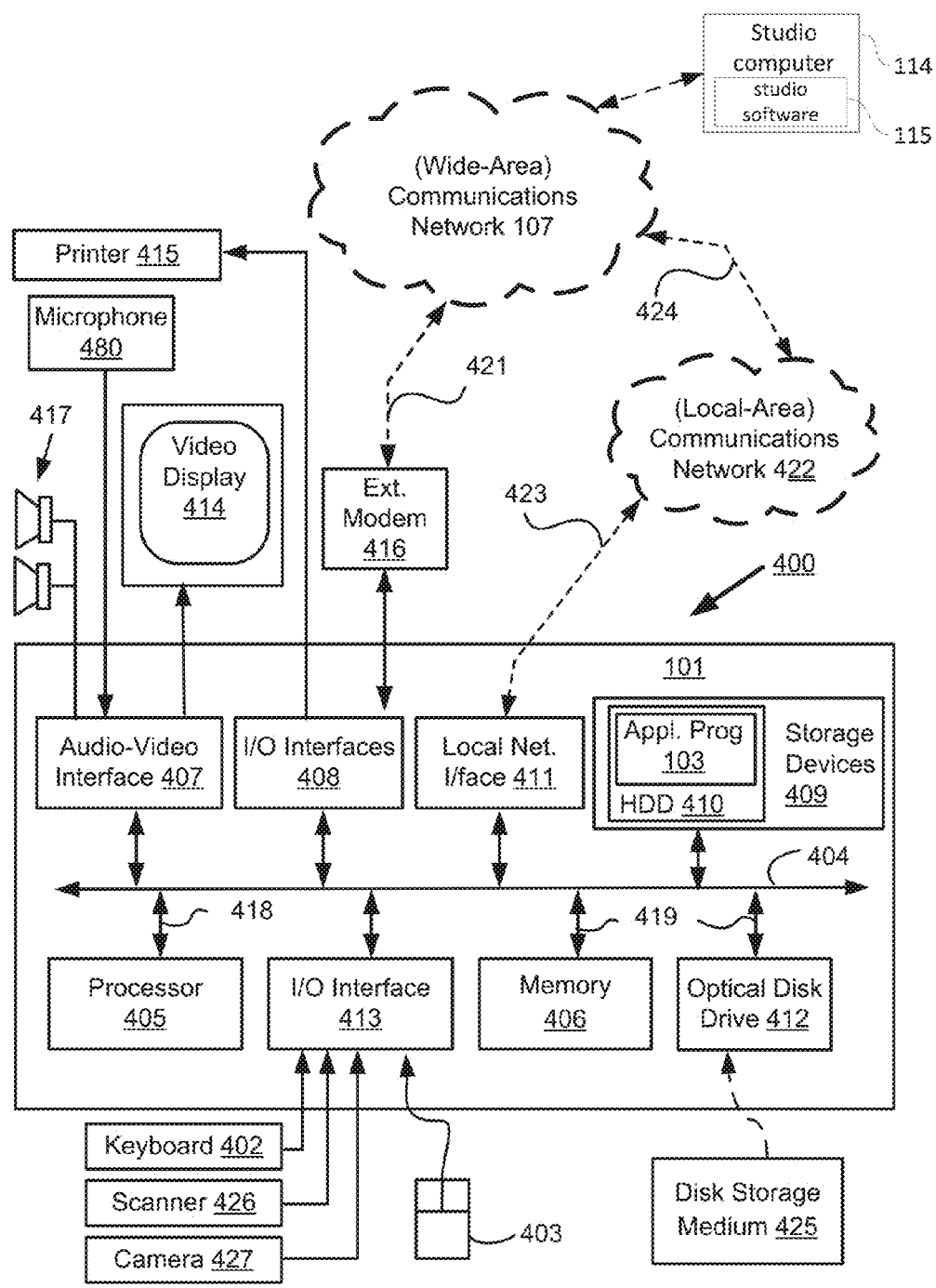
FIGS. 4A and 4B form a schematic block diagram of a general purpose computer system upon which arrangements described can be practiced.

The DPVSC service provider can control operation of the DPVSC arrangements via a user interface such as a keyboard 402 associated with the DPVSC server 101 (eg see FIG. 4A). Alternatively, the DPVSC service provider may use a portable terminal 132 which communicates with the DPVSC server 101 over the communication network 107 in order to perform various control operations. The portable terminal 132 can run a special purpose DPVSC application in order to communicate with the DPVSC server 101. Alternately, the portable terminal 132 can run a browser application to communicate with suitable software running on the DPVSC server 101.

A studio operator (not shown can edit the downloaded daily fitness information 213 via a user interface such as a keyboard (not shown) which communicates with the studio computer 114. Alternatively, the studio operator can use a portable terminal 125 in order to effect such editing operations. The portable terminal 125 can run a special purpose DPVSC application in order to communicate with the studio computer 114. Alternately, the portable terminal 125 can run a browser application to communicate with suitable software running on the studio computer 114.

As described hereinafter in more detail in regard to FIG. 3, the studio operator (not shown) downloads the current studio-specific fitness information 213 into a studio database 124. The studio operator can modify the downloaded fitness information 213 prior to communicating the fitness information 213 to the studio displays 117, 119, 123. Once the fitness information 213, or an edited version thereof, is communicated to the aforementioned displays, users of the studio can commence their exercise routines, as directed by information displayed on the aforementioned displays 117, 119, 123.

The DPVSC server 101 executes the DPVSC software 103 and communicates, as depicted by a connection 102, with the communication network 107. The server database 105, which stores the multi-period fitness library 104, communicates with the communication network 107 as depicted by a connection 106. The database 128, storing the studio information 129 which includes at least the initial registration date each studio registered with the DPVSC arrangement, communicates with the network 107 as depicted by a connection 130. The remote studio 109 communicates with the communication network 107 as depicted by a connection 108. The portable terminal 125 executing the studio software 127 communicates with the network 107 as depicted by a connection 126. The portable terminal 132 communicates with the network 107 as depicted by a connection 133. The studio 111, by means of the studio computer 114 which executes the studio software 115, communicates with the network 107 as depicted by a connection 110. The studio computer 114 communicates with the local communication network 112 as depicted by a connection 113. The display 117 communicates with the network 112 as depicted by a connection 116. The set of display windows 119, 120, 121 communicate with the network 112 as depicted by a connection 118. The display 123 communicates with the network 112 as depicted by a connection 122.

Figure 4B:
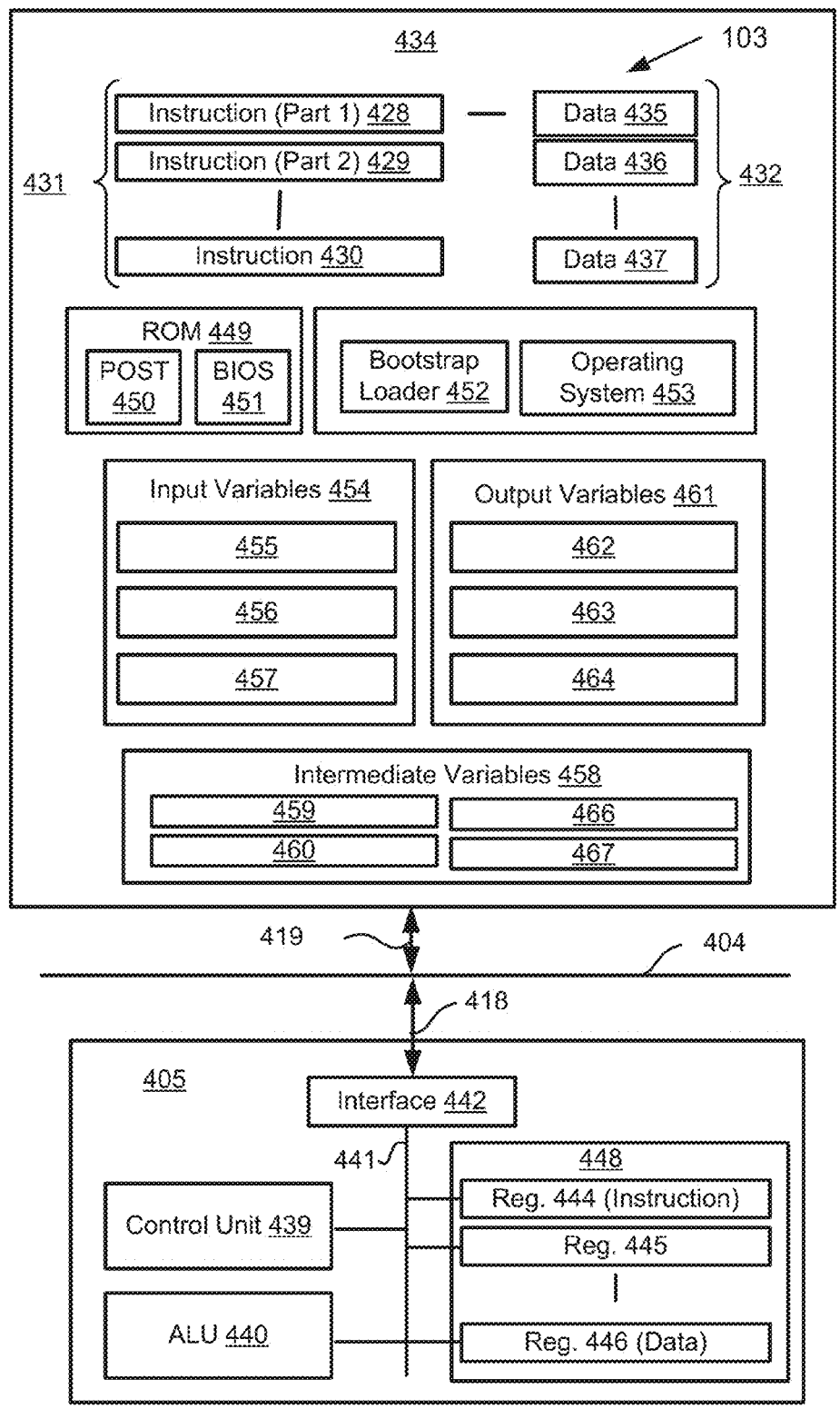

FIGS. 4A and 4B depict a general-purpose computer system 400, upon which the various arrangements described can be practiced.

As seen in FIG. 4A, the computer system 400 includes: a computer module 101 acting as the DPVSC server; input devices such as a keyboard 402, a mouse pointer device 403, a scanner 426, a camera 427, and a microphone 480; and output devices including a printer 415, a display device 414 and loudspeakers 417. An external Modulator-Demodulator (Modem) transceiver device 416 may be used by the computer module 101 for communicating to and from a communications network 107 via a connection 421. The communications network 107 may be a wide-area network (WAN), such as the Internet, a cellular telecommunications network, or a private WAN. Where the connection 421 is a telephone line, the modem 416 may be a traditional "dial-up" modem. Alternatively, where the connection 421 is a high capacity (e.g., cable) connection, the modern 416 may be a broadband modem. A wireless modem may also be used for wireless connection to the communications network 107.

The server 101 typically includes at least one processor unit 405, and a memory unit 406. For example, the memory unit 406 may have semiconductor random access memory (RAM) and semiconductor read only memory (ROM). The server 101 also includes an number of input/output (I/O) interfaces including: an audio-video interface 407 that couples to the video display 414, loudspeakers 417 and microphone 480; an I/O interface 413 that couples to the keyboard 402, mouse 403, scanner 426, camera 427 and optionally a joystick or other human interface device (not illustrated); and an interface 408 for the external modem 416 and printer 415. In some implementations, the modem 416 may be incorporated within the computer module 101, for example within the interface 408. The computer module 101 also has a local network interface 411, which permits coupling of the computer system 400 via a connection 423 to a local-area communications network 422, known as a Local Area Network (LAN). As illustrated in FIG. 4A, the local communications network 422 may also couple to the wide network 107 via a connection 424, which would typically include a so-called "firewall" device or device of similar functionality. The local network interface 411 may comprise an Ethernet circuit card, a Bluetooth® wireless arrangement or an IEEE 802.11 wireless arrangement; however, numerous other types of interfaces may be practiced for the interface 411.

The I/O interfaces 408 and 413 may afford either or both of serial and parallel connectivity, the former typically being implemented according to the Universal Serial Bus (USB) standards and having corresponding USB connectors (not illustrated). Storage devices 409 are provided and typically include a hard disk drive (HDD) 410. Other storage devices such as a floppy disk drive and a magnetic tape drive (not illustrated) may also be used. An optical disk drive 412 is typically provided to act as a non-volatile source of data. Portable memory devices, such optical disks (e.g., CD-ROM, DVD, Blu-Ray Disc™), USB-RAM, portable, external hard drives, and floppy disks, for example, may be used as appropriate sources of data to the system 400.

The components 405 to 413 of the computer module 101 typically communicate via an interconnected bus 404 and in a manner that results in a conventional mode of operation of the computer system 400 known to those in the relevant art. For example, the processor 405 is coupled to the system bus 404 using a connection 418. Likewise, the memory 406 and optical disk drive 412 are coupled to the system bus 404 by connections 419. Examples of computers on which the described arrangements can be practised include IBM-PC's and compatibles, Sun Sparcstations, Apple Mac™ or a like computer systems.

Figure 2:
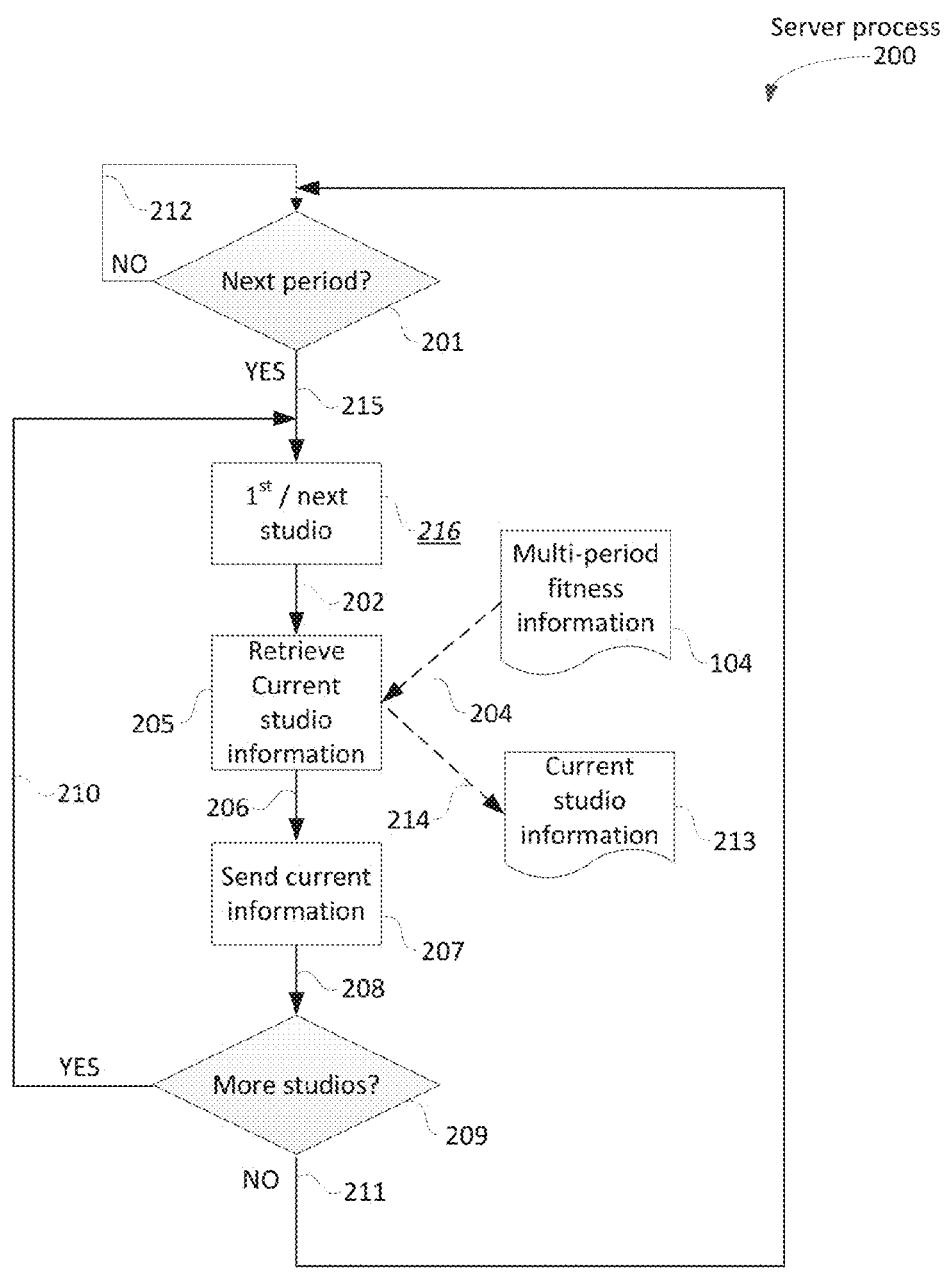
FIG. 2 is a flow chart illustrating one example of a process that can be performed by a DPVSC server.
Figure 3:
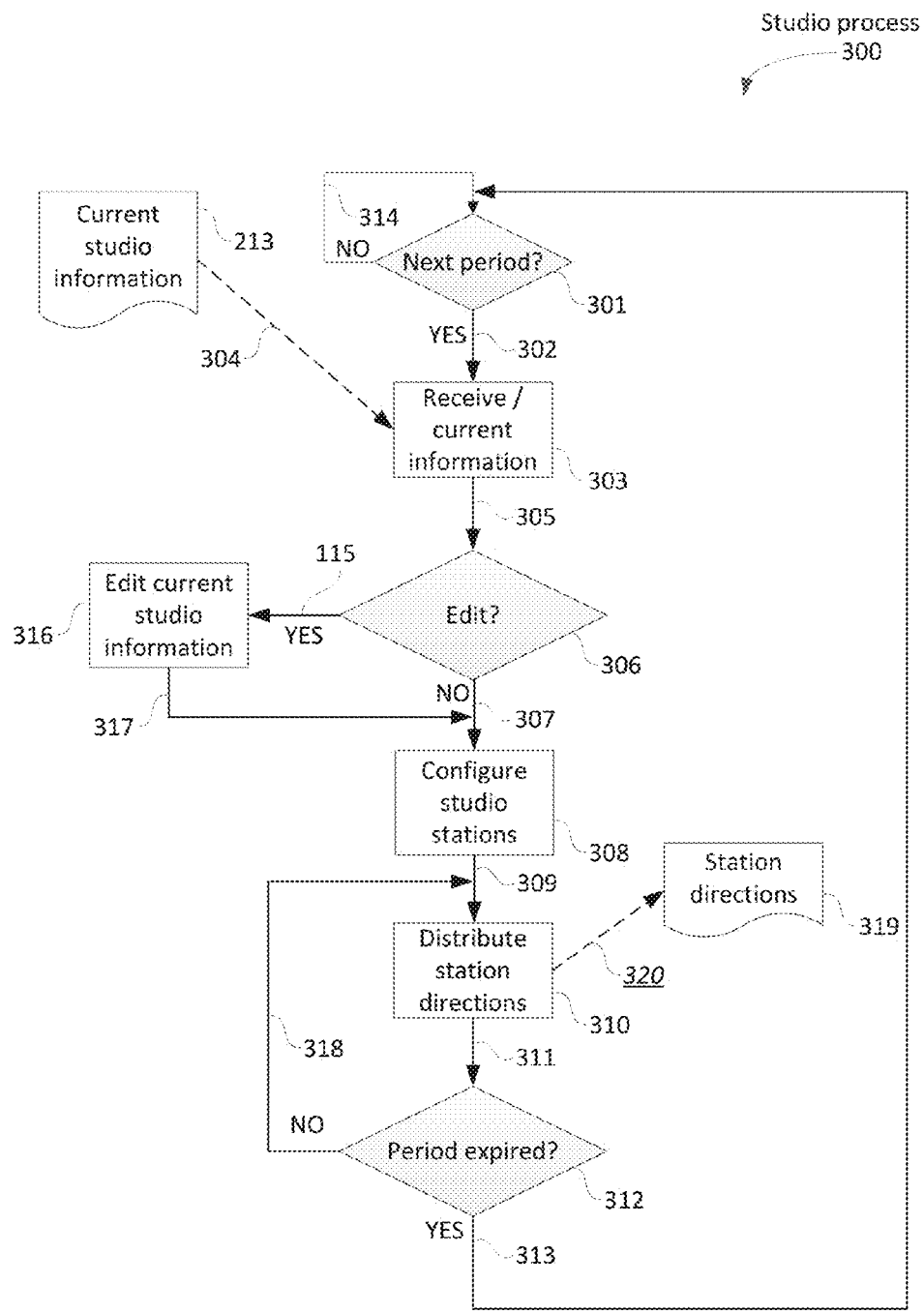
FIG. 3 is a flow chart illustrating an example of a process performed by a studio computer in a DPVSC arrangement.

The DPVSC methods may be implemented using the computer system 400 wherein the processes of FIGS. 2 and 3, to be described, may be implemented as one or more software application programs 103 executable within the computer system 400. In particular, the steps of the DPVSC method are effected by instructions 431 (see FIG. 4B) in the software 103 that are carried out within the computer system 400. The software instructions 431 may be formed as one or more code modules, each for performing one or more particular tasks. The software may also be divided into two separate parts, in which a first part and the corresponding code modules performs the DPVSC methods and a second part and the corresponding code modules manage a user interface between the first part and the user.

The software may be stored in a computer readable medium, including the storage devices described below, for example. The software is loaded into the computer system 400 from the computer readable medium, and then executed by the computer system 400. A computer readable medium having such software or computer program recorded on the computer readable medium is a computer program product. The use of the computer program product in the computer system 400 preferably effects an advantageous DPVSC apparatus.

The software 103 is typically stored in the HDD 410 or the memory 406. The software is loaded into the computer system 400 from a computer readable, medium, and executed by the computer system 400. Thus, for example, the software 103 may be stored on an optically readable disk storage medium (e.g., CD-ROM) 425 that is read by the optical disk drive 412. A computer readable, medium having such software or computer program recorded on it is a computer program product. The use of the computer program product in the computer system 400 preferably effects a DPVSC apparatus.

In some instances, the application programs 103 may be supplied to the user encoded on one or more CD-ROMs 425 and read via the corresponding drive 412, or alternatively may be read by the user from the networks 107 or 422. Still further, the software can also be loaded into the computer system 400 from other computer readable media. Computer readable storage media refers to any non-transitory tangible storage medium that provides recorded instructions and/or data to the computer system 400 for execution and/or processing. Examples of such storage media include floppy disks, magnetic tape, CD-ROM, DVD, Blu-Ray™ Disc, a hard disk drive, a ROM or integrated circuit, USB memory, a magneto-optical disk, or a computer readable card such as a PCMCIA card and the like, whether or not such devices are internal or external of the computer module 101. Examples of transitory or non-tangible computer readable transmission media that may also participate in the provision of software, application programs, instructions and/or data to the computer module 101 include radio or infra-red transmission channels as well as a network connection to another computer or networked device, and the Internet or Intranets including e-mail transmissions and information recorded on Websites and the like.

The second part of the application programs 103 and the corresponding code modules mentioned above may be executed to implement one or more graphical user interfaces (GUIs) to be rendered or otherwise represented upon the display 414. Through manipulation of typically the keyboard 402 and the mouse 403, a user of the computer system 400 and the application may manipulate the interface in a functionally adaptable manner to provide controlling commands and/or input to the applications associated with the GUI(s). Other forms of functionally adaptable user interfaces may also be implemented, such as an audio interface utilizing speech prompts output via the loudspeakers 417 and user voice commands input via the microphone 480.

FIG. 4B is a detailed schematic block diagram of the processor 405 and a "memory" 434. The memory 434 represents a logical aggregation of all the memory modules (including the HDD 409 and semiconductor memory 406) that can be accessed by the computer module 101 in FIG. 4A.

When the computer module 101 is initially powered up, a power-on self-test (POST) program 450 executes. The POST program 450 is typically stored in a ROM 449 of the semiconductor memory 406 of FIG. 4A. A hardware device such as the ROM 449 storing software is sometimes referred to as firmware. The POST program 450 examines hardware within the computer module 101 to ensure proper functioning and typically checks the processor 405, the memory 434 (409, 406), and a basic input-output systems software (BIOS) module 451, also typically stored in the ROM 449, for correct operation. Once the POST program 450 has run successfully, the BIOS 451 activates the hard disk drive 410 of FIG. 4A. Activation of the hard disk drive 410 causes a bootstrap loader program 452 that is resident on the hard disk drive 410 to execute via the processor 405. This loads an operating system 453 into the RAM memory 406, upon which the operating system 453 commences operation. The operating system 453 is a system level application, executable by the processor 405, to fulfil various high level functions, including processor management, memory management, device management, storage management, software application interface, and generic user interface.

The operating system 453 manages the memory 434 (409, 406) to ensure that each process or application running on the computer module 101 has sufficient memory in which to execute without colliding with memory allocated to another process. Furthermore, the different types of memory available in the system 400 of FIG. 4A must be used properly so that each process can run effectively. Accordingly, the aggregated memory 434 is not intended to illustrate how particular segments of memory are allocated (unless otherwise stated), but rather to provide a general view of the memory accessible by the computer system 400 and how such is used.

As shown in FIG. 4B, the processor 405 includes a number of functional modules including a control unit 439, an arithmetic logic unit (ALU) 440, and a local or internal memory. 448, sometimes called a cache memory. The cache memory 448 typically includes a number of storage registers 444-446 in a register section. One or more internal busses 441 functionally interconnect these functional modules. The processor 405 typically also has one or more interfaces 442 for communicating with external devices via the system bus 404, using a connection 418. The memory 434 is coupled to the bus 404 using a connection 419.

The application program 103 includes a sequence of instructions 431 that may include conditional branch and loop instructions. The program 103 may also include data 432 which is used in execution of the program 103. The instructions 431 and the data 432 are stored in memory locations 428, 429, 430 and 435, 436, 437, respectively. Depending upon the relative size of the instructions 431 and the memory locations 428-430, a particular instruction may be stored in a single memory location as depicted by the instruction shown in the memory location 430. Alternately, an instruction may be segmented into a number of parts each of which is stored in a separate memory location, as depicted by the instruction segments shown in the memory locations 428 and 429.

In general, the processor 405 is given a set of instructions which are executed therein. The processor 1105 waits for a subsequent input, to which the processor 405 reacts to by executing another set of instructions. Each input may be provided from one or more of a number of sources, including data generated by one or more of the input devices 402, 403, data received from an external source across one of the networks 107, 402, data retrieved from one of the storage devices 406, 409 or data retrieved from a storage medium 425 inserted into the corresponding reader 412, all depicted in FIG. 4A. The execution of a set of the instructions may in some cases result in output of data. Execution may also involve storing data or variables to the memory 434.

The disclosed DPVSC arrangements use input variables 454, which are stored in the memory 434 in corresponding memory locations 455, 456, 457. The DPVSC arrangements produce output variables 461, which are stored in the memory 434 in corresponding memory locations 462, 463, 464, Intermediate variables 458 may be stored in memory locations 459, 460, 466 and 467.

Referring to the processor 405 of FIG. 4B, the registers 444, 445, 446, the arithmetic logic unit (ALU) 440, and the control unit 439 work together to perform sequences of micro-operations needed to perform "fetch, decode, and execute" cycles for every instruction in the instruction set making up the program 103. Each fetch, decode, and execute cycle comprises;

a fetch operation, which fetches or reads an instruction 431 from a memory location 428, 429, 430;
a decode operation in which the control unit 439 determines which instruction has been fetched; and
an execute operation in which the control unit 439 and/or the ALU 440 execute the instruction.

Thereafter, a further fetch, decode, and execute cycle for the next instruction may be executed. Similarly, a store cycle may be performed by which the control unit 439 stores or writes a value to a memory location 432.

Each step or sub-process in the processes of FIGS. 2 and 3 is associated with one or more segments of the program 103 and is performed by the register section 444, 445, 447, the ALU 440, and the control unit 439 in the processor 405 working together to perform the fetch, decode, and execute cycles for every instruction in the instruction set for the noted segments of the program 103.

The DPVSC method may alternatively be implemented in dedicated hardware such as one or more integrated circuits performing the DPVSC functions or sub functions. Such dedicated hardware may include graphic processors, digital signal processors, or one or more microprocessors and associated memories.

FIG. 2 is a flow chart illustrating one example of a process 200 that can be performed by the DPVSC server 101. The process 200 commences with a test step 201, performed by the processor 405 executing DPVSC software 103, in order to determine whether it is time to download the next respective daily fitness information file to the various studios 109, 111 that are enrolled with the DPVSC service. If this is not the case, the process 200 follows a NO arrow 212 back to the step 201. If, on the other hand, it is time to download the next daily fitness information, then the process 200 follows a YES arrow 215 to a step 216.

At the beginning of the download for each day, the step 216 contains an index pointing to a date currently ascribed to the studio that has the earliest registration date in a list of studios receiving the DPVSC service. Thereafter, following an arrow 202 in a step 205, performed by the processor 405 executing DPVSC software 103, the server 101 periodically retrieves the studio specific current information 213, indexed by the date set by the step 216, from the multi-period fitness library 204 that is stored on the server database 105. Thereafter, following an arrow 206, the server 101 sends the current fitness information 213 to all studios that enrolled with the DPVSC service on the same date, as recorded by the studio information 129. Thereafter, following an arrow 208, a test step 209 determines if there are further studios that have not yet received their daily download. If this is the case, then the process 200 follows a YES arrow 210 back to the step 216 which increments to the next date upon which a studio registered with the DPVSC service. If, on the other hand, there are no more studios to receive the daily download, then the process 200 follows a NO arrow 211 back to the test step 201. Furthermore, the index associated with the step 216 is set to the same date used on the current day plus one day.

FIGS. 10A and 10B respectively depict examples of the multi-period fitness library 104 and a current studio program 213 extracted from the multi-period fitness library.

FIG. 10A shows that the multi-period fitness library 104 is made up of a succession of studio information program files 1007, 1008, 1009, 1010 . . . , 1011, . . . . Each item of studio information, such as 1007, is also associated with a particular date 1014. In the case of the studio information 1007, the date associated with that item is 17 Jan. 2014. Successive items in the multi-period fitness library are associated with successive dates. The multi-period fitness library is, in one DPVSC example, constructed out over a 2 to 3 year period. The multi-period fitness library 104 is typically continuously added to so that new exercise routines are added to the library 104 in an ongoing manner.

When a studio first registers with the DPVSC service, the first daily download of current studio information 213 that the studio receives is dictated by the date of registration. Thus, for example, if the studio 109 enrolled with the DPVSC service on 18 Jan. 2014, then the first daily download of current studio information 213 is the studio information 1008, as depicted by a dashed arrow 1012. In contrast, if the studio 111 registered with the DPVSC service on 20 Jan. 2014, then the first daily download of current studio information 213 which the studio 111 receives is the studio information 1010, as depicted by a dashed arrow 1013. In this manner, studios which enroll with the DPVSC service on different dates commence at a different point in the multi-period fitness library 104, Alternately, all studios in the DPVSC arrangement can receive identical downloads of current studio information 213. This can arise for promotional purposes for example. Alternately, the current studio information 213 for each studio can be retrieved by the server in the step 205 from the library 104 in any other order as may be desired.

FIG. 10B shows current studio information 213, and it is evident that the information 213 is made up of exercise parameters associated with a number of different information segments. One segment 1001 described hereinafter in more detail in regard to FIG. 8, contains the name of a current workout. Another segment 1002, described hereinafter in more detail in regard to FIGS. 8, 5A, 5B, GA, 6B, 7A and 7B contains the locations of the exercise stations within the studio for the day in question, as well as equipment associated with each station, Another segment 1003 contains one or more music playlists for the studio for the day in question. Another information segment 1004, described hereinafter in more detail in regard to FIG. 12, contains timer parameters for each station in the studio. Another information segment 1005, described hereinafter in more detail with reference to FIG. 12, contains one or more video files for each exercise station. An information segment 1006, described hereinafter in more detail with regard to FIG. 8, contains a list of exercises for each exercise station.

FIG. 3 is a flow chart illustrating an example of a process 300 performed by a studio computer such as 114 in a DPVSC arrangement. The process 300 commences with a step 301, performed by a processor (not shown) in the computer 114, as directed by a software application (not shown) running on the computer 114, in which the studio computer 114 determines if it is time to receive a new daily download from the server 101. If this is not the case, then the process 300 follows an NO arrow 314 back to the step 301. If, on the other hand, it is time to receive a new download, then the process 300 follows a YES arrow 302 to a step 303 as depicted by an arrow 302. In the step 303, performed by a processor (not shown) in the computer 114, as directed by a software application (not shown) running on the computer 114, the studio computer 104 periodically receives as depicted by a dashed arrow 304, the new daily studio information 213. Control then follows an arrow 305 to a decision step 306 in which the operator of the studio 111 (not shown) decides whether or not to edit the current studio information 213 that has been downloaded by the server 101. If editing is desired, then control follows a YES arrow 115 to a step 316 in which the studio operator edits the downloaded information 213 using user interface modules at the studio computer 114. Control then follows an arrow 317 to a step 308. Returning to the decision step 306, if the received current studio information 213 does not require editing, then control follows an NO arrow 307 to the step 308.

In the step 308 studio staff configure the studio exercise stations 128, 129 throughout the studio in question in accordance with the current studio information 213 or the edited version thereof.

The configuration of the studio stations arranged in accordance with the step 308 has a number of different aspects. Once of these, described hereinafter in more detail with respect to FIGS. 5A, 5B, 6A, 6B, 7A and 7B relate to physically locating the exercise stations around the studio in question in a particular physical layout. Another aspect relates to equipment which may be associated with each station, described hereinafter in more detail in regard to FIGS. 8 and 9.

Returning to FIG. 3, the process 300 then follows an arrow 309 to a step 310. In the step 310, performed by a processor (not shown) in the computer 114, as directed by a software application (not shown) running on the computer 114, the studio computer 114 distributes station information, derived from the downloaded current studio information 213 or the edited version thereof, to the displays 117, 119 . . . .

The studio is now ready for users thereof to commence their exercise routines, and the process 300 follows an arrow 311 to a decision step 312, In the step 312, performed by a processor (not shown) in the computer 114, as directed by a software application (not shown) running on the computer 114, the studio computer 114 determines if the current exercise daily period has expired. The studio will continue operating until the step 312 determines that the end of the day has arrived. If the end of the day has not yet arrived, then the process 300 follows an NO arrow 318 back to the step 310, In this manner, the current studio information is presented, on a per-exercise station basis, throughout the day. If, on the other hand, the step 312 determines that the daily exercise period has expired, then the process 300 follows a YES arrow 313 back to the step 301. At this point, the information being presented at the various exercise stations is shut down.

Figure 12:
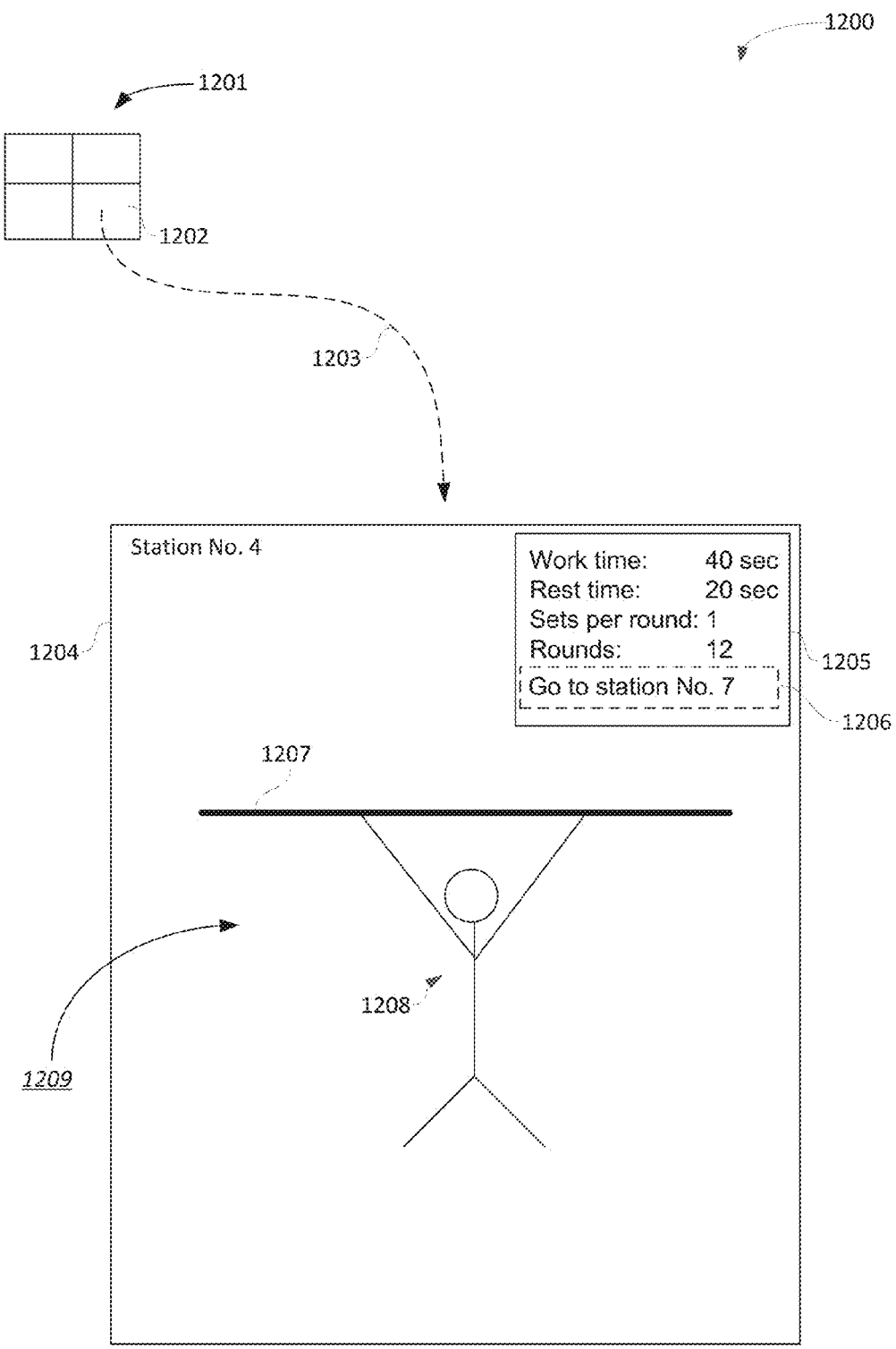
FIG. 12 illustrates an example of a display screen associated with an exercise station in a studio according to a DPVSC arrangement.

FIG. 12 illustrates an example 1200 of a display screen 1204 associated with an exercise station in the studio 111 according to a DPVSC arrangement. In the example shown, the station associated with the display 1204 is station No. 4. In FIG. 12 the display 1204 is actually a display window 1202 in a larger display 1201.

Once the step 310 in the process 300 (see FIG. 3) commences distribution of station directions to the various displays, a user at the station No. 4 sees a video presentation 1209 on the display 1204. The video presentation 1209 demonstrates a particular exercise that the user of station No. 4 is to perform at the station in question. In the illustration 1200 a person 1208, shown in stick figure form, is performing chin-ups using the horizontal bar 1207. Presentation of information 1205 at an upper right hand corner of the display 1204 indicates that the "work time" during which the user is to perform the chin-ups is a 40 second period. Subsequently, the user is to observe a rest time of 20 seconds. The user is to perform one set of chin-ups according to the aforementioned work/rest times per "set", and is to perform 12 rounds in total. This means, in one example, that the user is to perform chin-ups for 40 seconds and then rest for 20 seconds, after which, in accordance with an instruction 1206, the user is to go to station No. 7 and follow the instructions on the associated display at that station. At some point, the user will be directed back to the present station No. 4, at which time the user will repeat the chin-ups for the work time of 40 seconds and the rest time of 20 seconds. The user will repeat this repetition 12 times during the present exercise session.

Figure 11:
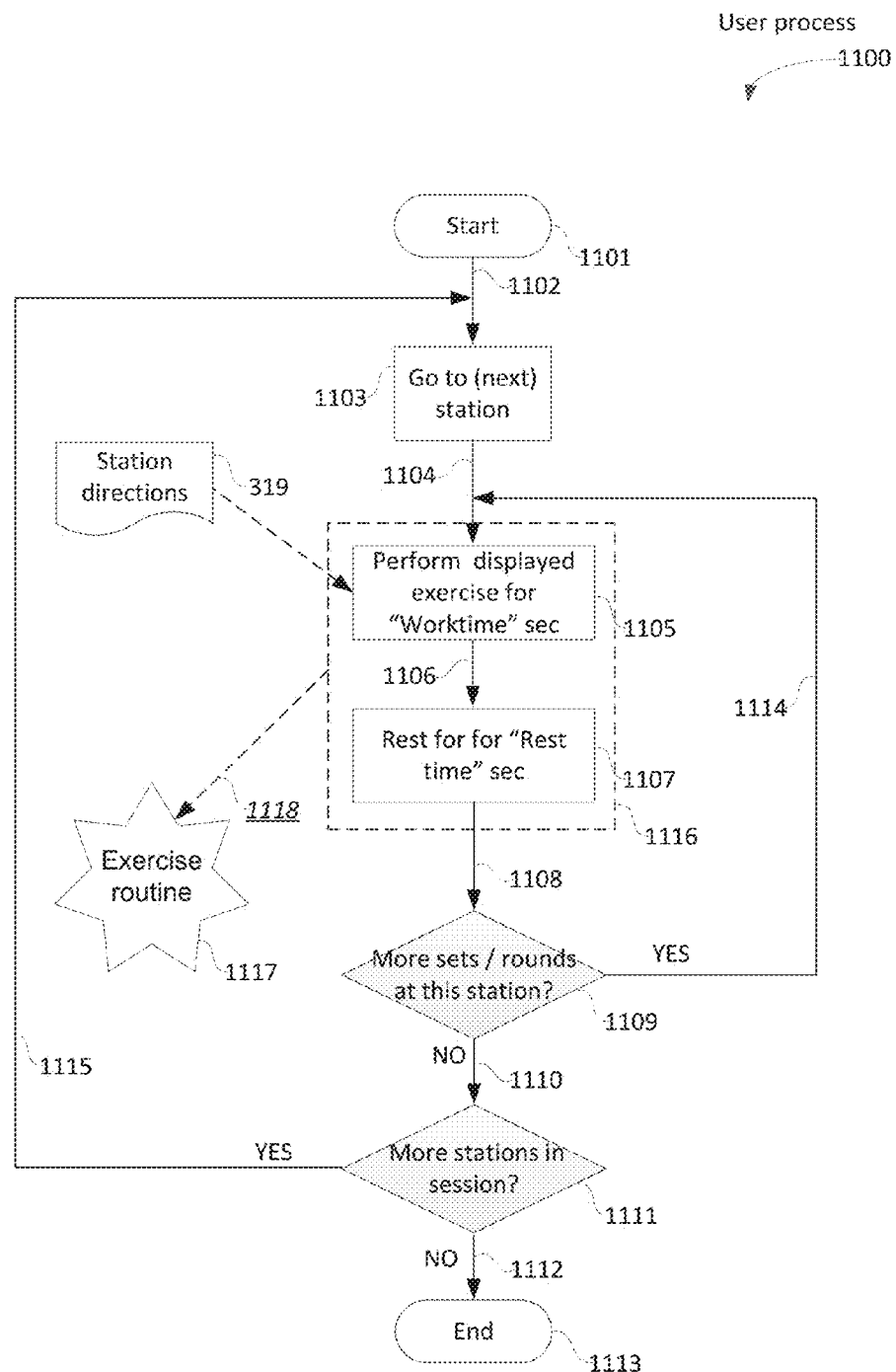
FIG. 11 is a flow chart showing one example of a process used by a user of the DPVSC arrangement.

FIG. 11 is a flow chart showing one example of a process 1100 used by a user of the DPVSC arrangement. The process 1100 commences with a start step 1101 and control then follows an arrow 1102 to a step 1103 in which the user goes to a first station in the studio. The user can either pick a random station to which to go for this initial exercise session, or can be directed there by a personal trainer. Control then follows an arrow 1104 to a step 1105 in which the user performs the displayed exercise for "work time" seconds in accordance with station directions 319 (also referred to as exercise routines) that are presented on the display 1204 (see FIG. 12), Control then follows an arrow 1106 to a process 1107 in which the user rests for "rest time" seconds in accordance with the directions 1205 on the display 1204. The aforementioned performance of the exercise and the rest period associated therewith constitute, as depicted by a dashed arrow 1118, an exercise routine 1117 that the user performs at the station in question.

After performing the exercise and rest periods indicated by the station directions 319, the process 1100 follows an arrow 1108 to a step 1109 which determines whether sets/rounds are to be performed at the present station. This is typically determined by the station directions 1205 presented on the display 1204. If further sets/rounds at the present station are to be performed, then control follows a YES arrow 1114 back to the step 1105. If, on the other hand, there are no further sets/rounds to be performed at the present station, then control follows a NO arrow 1110 to a step 1111. The step 1111 determines whether there are further stations for the user to use during the present exercise session. If this is the case, then control follows a YES arrow 1115 which directs control back to the step 1103 in which the user goes to the next station, as indicated by the direction 1206 in FIG. 12, if, on the other hand, there are no more stations in the present session, then it is time for the user to go home and control follows an arrow 1112 (being a NO arrow) to a termination step 1113.

Figure 5A:
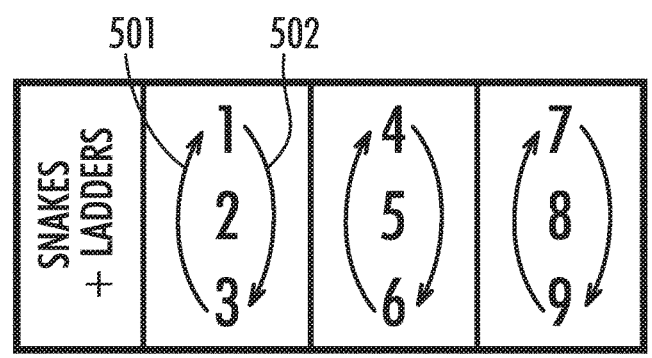
FIG. 5A illustrates a "snakes and ladders" configuration of exercise stations, and associated station sequencing, according to a DPVSC arrangement.

FIG. 5A illustrates a "snakes and ladders" configuration of exercise stations, and associated station sequencing, according to a DPVSC arrangement. The station sequencing, depicted by arrows such as 501, 502, direct station users how to progress from station to station. FIG. 5A depicts a "snakes and ladders" pattern in which a user progresses from station 1 to station 3 and back to station 1 in a cyclical pattern. Similar directions are provided to a user of station 4 who moves to station 6 and then back to station 4 and so on.

Figure 5B:
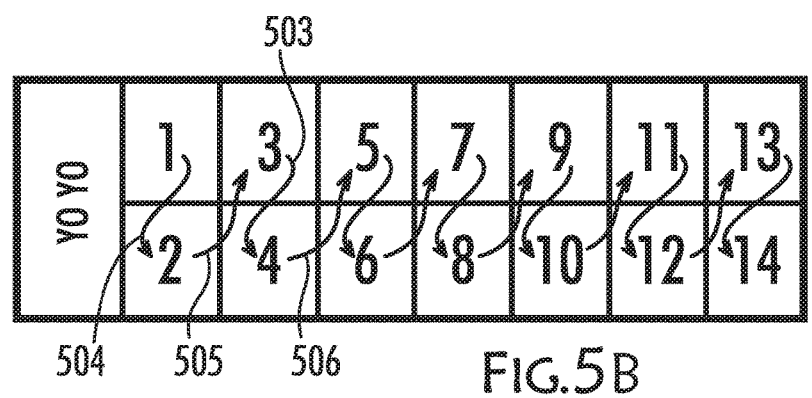
FIG. 5B illustrates a "yo yo" configuration of exercise stations, and associated station sequencing, according to a DPVSC arrangement.

FIG. 5B illustrates a "yo yo" configuration of exercise stations, and associated station sequencing, according to a DPVSC arrangement, Stations are distributed throughout the studio as depicted, and users move from station 1 to station 2 then to station 3 and then station 4, and so on as shown by arrows 502, 505, 503 and so on in the figure.

Figure 6A:
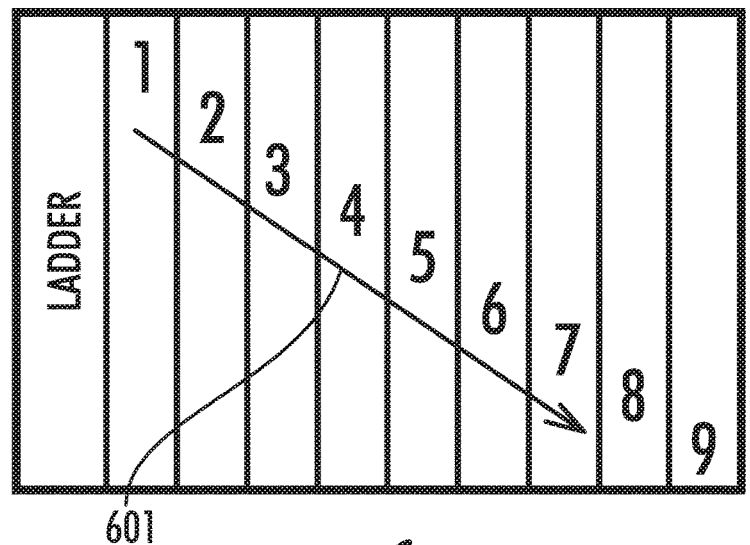
FIG. 6A illustrates a "ladder" configuration of exercise stations, and associated station sequencing, according to a DPVSC arrangement.

FIG. 6A illustrates a "ladder" configuration of exercise stations, and associated station sequencing, according to a DPVSC arrangement, Stations are distributed in a diagonal linear fashion across the studio. Users of the stations progress in a linear fashion from station 1 to station 2 to station 3 and so on as depicted by an arrow 601.

Figure 6B:
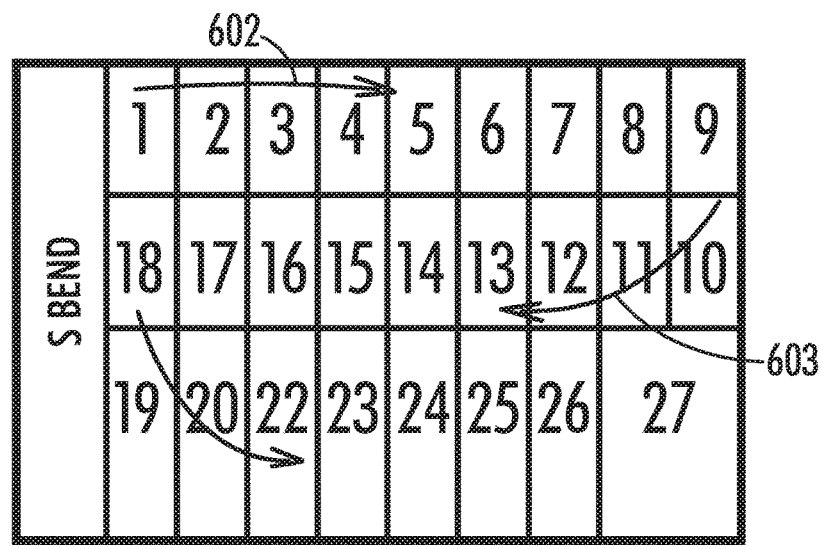
FIG. 6B illustrates an "S bend" configuration of exercise stations, and associated station sequencing, according to a DPVSC arrangement.

FIG. 6B illustrates an "S bend" configuration of exercise stations, and associated station sequencing, according to a DPVSC arrangement, Exercise stations are distributed throughout the studio as indicated, Users move in a station hopping configuration from station 1 to station 5 and so on.

Figure 7A:
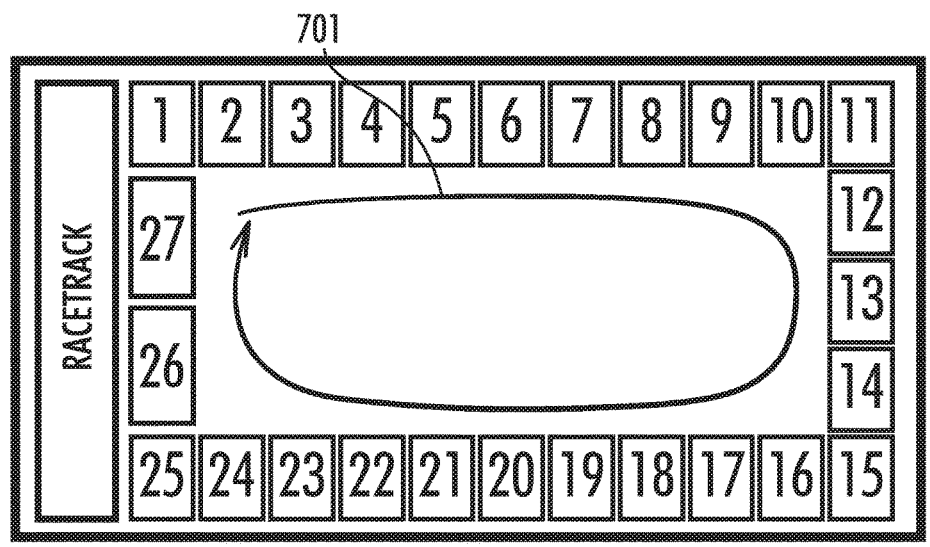
FIG. 7A illustrates a "race track" configuration of exercise stations, and associated station sequencing, according to a DPVSC arrangement.

FIG. 7A illustrates a "race track" configuration of exercise stations, and associated station sequencing, according to a DPVSC arrangement. Exercise stations are distributed throughout the studio in the manner shown, Station users progress in a linear fashion from station 1 to station 2, to station 3, and so on as depicted by an arrow 701.

Figure 7B:
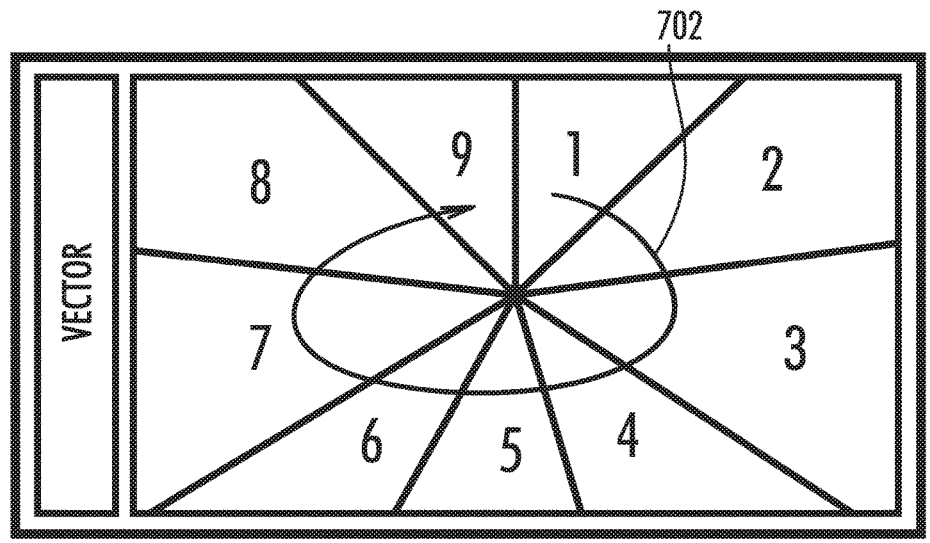
FIG. 7B illustrates a "vector" configuration of exercise stations, and associated station sequencing, according to a DPVSC arrangement.

FIG. 7B illustrates a "vector" configuration of exercise stations, and associated station sequencing, according to a DPVSC arrangement. Exercise stations are distributed throughout the studio in the manner shown. Station users progress in a circular fashion from station 1 to station 2, to station 3 and so on as depicted by an arrow 702.

Figure 8:
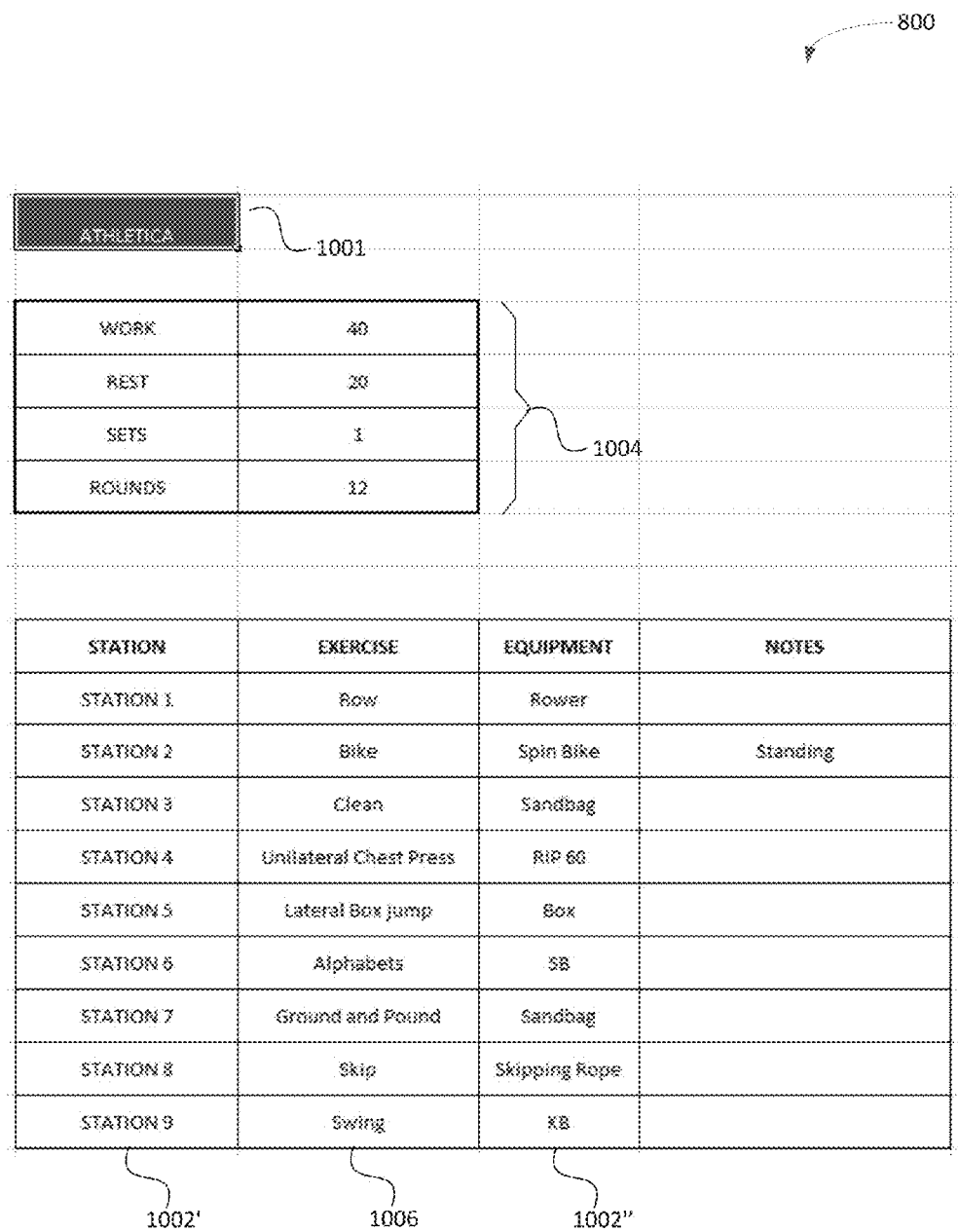
FIG. 8 illustrates information specifying an example, entitled "Athletica", of a daily exercise session.

FIG. 8 illustrates information 800 specifying an example, entitled "Athletics", of a daily exercise session. FIG. 8 illustrates only part of the daily current studio information 213, as illustrated by FIG. 10B. FIG. 8 illustrates information 800 specifying an example, entitled "Athletica", of a daily exercise session contained in the current studio information 213. The name of the workout (see FIG. 10B) is referenced at 1001, the name being "Athletics". The association between exercise stations and equipment, if any, is depicted at 1002' and 1002", A list of exercises associated with each station is referenced by 1006.

Figure 9:
FIG. 9 illustrates information specifying an example, entitled "Athletica", of a daily exercise session.

FIG. 9 depicts another example 900 of information such as that depicted in FIG. 8.

Figure 13:
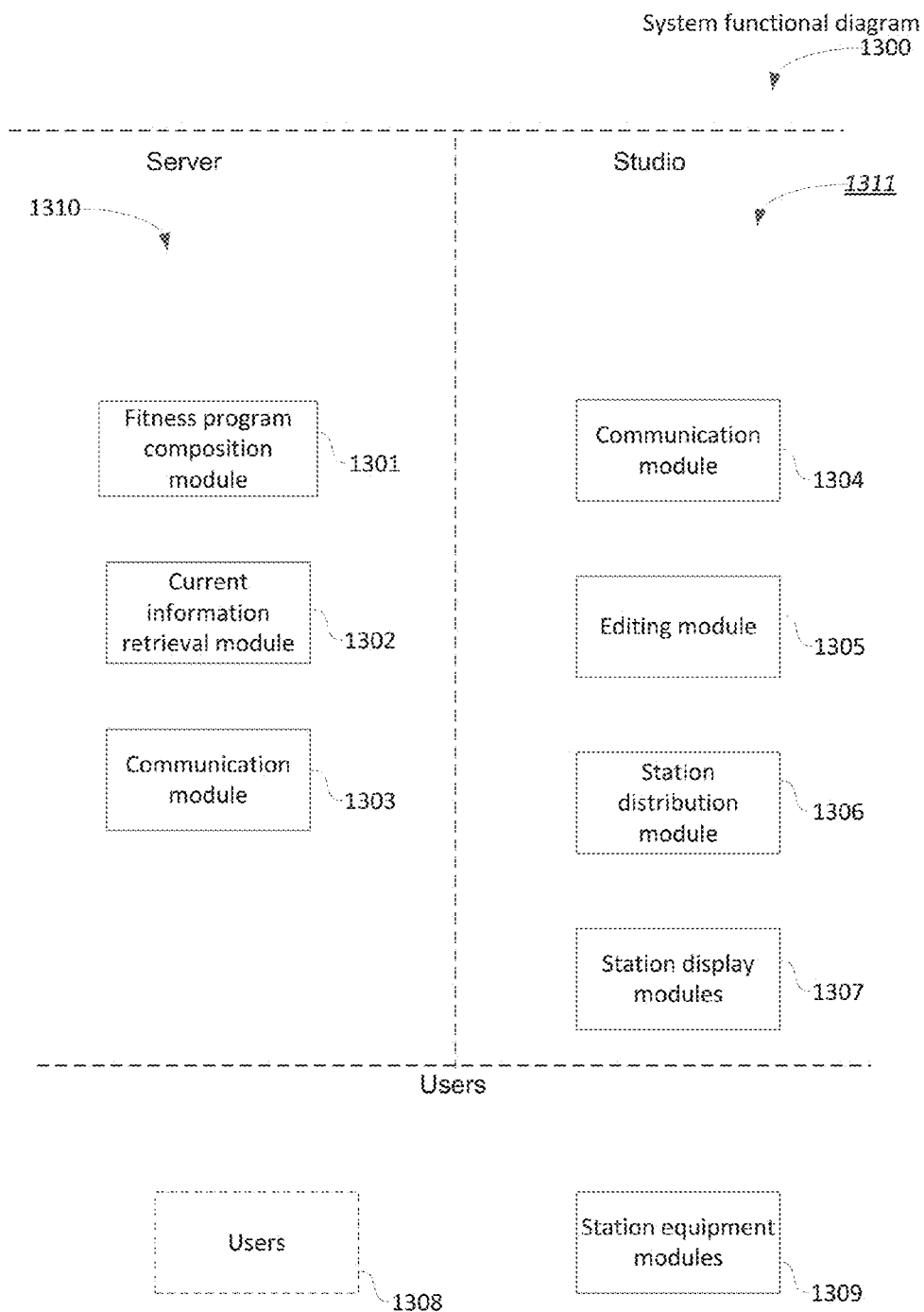
FIG. 13 shows an example of system functional modules used in a DPVSC arrangement.

FIG. 13 shows an example 1300 of system functional modules used in a DPVSC arrangement. The functional modules may be distributed between the server 101, the studio computer 114 and the users of the studios. The server contains a fitness program composition module 1301 which enables fitness experts to construct the multi-period fitness library 104, This module can reside in the memory 406 of the server 101, as depicted in FIG. 4A. The server also comprises a current information retrieval module 1302 which performs the process 205 of retrieving current studio information 213 from the multi-period fitness library 104. Also incorporated in the server 101 is a communication module 1303 that is configured to communicate the current information 213 from the server 101 to the studio computers 114 as depicted by the process 207.

The studio computer 114 comprises a station communication module 1304 that is configured to perform the process 303 of receiving the current studio information 213, The studio computer 114 also comprises an editing module 1305 enabling studio operators to edit the received studio information 213 as depicted by the process 316. The editing module 1305 enables the studio operator to change some or all aspects of the received studio information 213 including the physical configuration of the stations (per FIGS. 5A and 5B for example), the timing parameters 1004, the equipment associated with each exercise station as depicted by 1002" and 1002', the exercises to be performed at each station as depicted by 1002' and 1006, the name of the workout 1001, the music playlists 1003, and the video files 1005.

The studio computer 114 also comprises a station distribution module 1306 that is configured to distribute the station directions as described in relation to the process 310 in FIG. 3. In this regard, the studio computer 114 can, in one DPVSC implementation, continuously steam information to the studio displays such as 117 on a continuous basis throughout the day. Alternatively, each display 117 can have a local processor and memory (not shown) to which station directions for the current day can be downloaded once only. Thereafter, the local processor and memory can present the downloaded information at the display 117 as required.

The studio also comprises the station display modules 1307 which in one DPVSC arrangement comprise only the displays such as 117. In an alternate DPVSC arrangement, the station display modules can also incorporate, together with the displays such as 117, associated memory and processors as noted before.

The DPVSC arrangement also includes station equipment modules 309, as depicted by 1002" in FIG. 8.

INDUSTRIAL APPLICABILITY

The arrangements described are applicable to the computer and data processing industries and particularly for the fitness industry.

The foregoing describes only some embodiments of the present invention, and modifications and/or changes can be made thereto without departing from the scope and spirit of the invention, the embodiments being illustrative and not restrictive.

The invention claimed is:

1. A computer implemented method for configuring and operating one or more fitness studios each comprising a plurality of exercise stations at which users perform associated exercise routines, each exercise station having an associated display, the method comprising, the steps of:
   periodically retrieving, by a server from a database, a studio information program file for a particular studio for a specified period, from a pre-prepared multi-period fitness library comprising a succession of studio information program files, wherein the studio information program file that is retrieved for a current period is different from a studio information program file that was retrieved for a previous period, thereby providing periodic variation of exercise programs;
   communicating, by the server to a studio computer associated with the particular studio, the retrieved studio information program file over a communications network;
   receiving, by the studio computer, the communicated studio information program file;
   periodically physically redistributing the exercise stations within the fitness studio dependent upon the received studio information program file; and
   communicating, by the studio computer to the exercise station displays, dependent upon the received studio information program file, station directions to users exercising at the stations for performing an exercise.

2. A method according to claim 1, wherein prior to the server retrieving the studio information program file for the specified period the method comprises the further steps of:
   constructing studio information program files for multiple periods;
   indexing the studio information program files with specified corresponding dates; and
   storing the studio information program files in the multi-period fitness library in the database.

3. A computer implemented method for configuring and operating a fitness studio comprising a plurality of exercise stations at which users perform associated exercise routines, each exercise station having an associated display, the method comprising the steps of:
   periodically receiving, by a studio computer, studio specific studio information for a specified period, from a pre-prepared multi-period fitness library comprising a succession of studio information program files, wherein the studio information program file that is retrieved for the specified period is different from a studio information program file that was retrieved for a previous period, thereby providing periodic variation of exercise programs, the library stored on a server database;
   periodically physically redistributing the exercise stations within the fitness studio dependent upon the received studio information program file; and
   communicating, by the studio computer to the exercise station displays, dependent upon the received studio information program file, station directions for users exercising at the stations for performing an exercise.

4. A method according to claim 3, wherein the studio information program file for the specified period comprises one or more of:
   a physical layout of the stations and any associated exercise equipment;
   video files demonstrating exercises to be performed at the stations; and
   exercise parameters for directing users of the stations for performing associated exercises.

5. A method according to claim 3, wherein the configuring step comprises repositioning the stations and associated equipment in the studio according to the physical layout.

6. A method according to claim 4, wherein the exercise parameters comprise one or more of:
   a duration parameter specifying a duration for performance of an exercise;
   a repetition parameter specifying a number of repetitions for performing the exercise;
   a rest parameter specifying a rest duration between repetitions; and
   an instruction directing a user of the station to another station when all exercise repetitions at the station are completed.

7. A system for configuring and operating a fitness studio comprising a plurality of exercise stations at which users perform associated exercise routines, each exercise station having an associated display, the system comprising:
- a station communication module for periodically receiving, by a studio computer from a server over a communications network, studio specific studio information program file for a specified period, including physical exercise station distribution information from a pre-prepared multi-period fitness library stored on a server database comprising a succession of studio information program files, wherein the studio information program file that is retrieved for a current period is different from a studio information program file that was retrieved for a previous period, thereby providing periodic variation of exercise programs;
- a station distribution module for communicating, by the studio computer to the exercise station displays, dependent upon the received studio information program file, station directions to users exercising at the stations for performing an exercise; and
- station display modules for displaying the station directions.

8. A non-transitory computer readable storage medium storing a computer executable program for directing one or more processors to perform a method for configuring and operating one or more fitness studios each comprising a plurality of exercise stations at which users perform associated exercise routines, each exercise station having an associated display, the method comprising, for each fitness studio, the steps of:
- periodically retrieving, by a server from a database, a studio information program file for the studio in question for a specified period, from a pre-prepared multi-period fitness library comprising a succession of studio information program files, wherein the studio information program file that is retrieved for a current period is different from a studio information program file that was retrieved for a previous period, thereby providing periodic variation of exercise programs;
- communicating, by the server to a studio computer, the retrieved studio information program file over a communications network;
- periodically receiving, by the studio computer, the retrieved studio information program file;
- periodically physically redistributing the exercise stations within the fitness studio dependent upon the received studio information program file; and
- communicating, by the studio computer to the exercise station displays, dependent upon the received studio information program file, station directions to users exercising at the stations for performing an exercise.

9. A non-transitory computer readable storage medium storing a computer executable program for directing one or more processors to perform a method for configuring and operating a fitness studio comprising a plurality of exercise stations at which users perform associated exercise routines, each exercise station having an associated display, the method comprising the steps of:
- periodically receiving, by a studio computer, studio specific studio information program file for a specified period, from a pre-prepared multi-period fitness library stored on a server database comprising a succession of studio information program files, wherein the studio information program file that is retrieved for a current period is different from a studio information program file that was retrieved for a previous period, thereby providing periodic variation of exercise programs;
- periodically physically redistributing the exercise stations within the fitness studio dependent upon the received studio information program file; and
- communicating, by the studio computer to the exercise station displays, dependent upon the received studio information program file, station directions for users exercising at the stations for performing an exercise.

* * * * *